United States Patent
Shalaby et al.

(10) Patent No.: US 8,936,784 B2
(45) Date of Patent: Jan. 20, 2015

(54) ABSORBABLE IN SITU GEL-FORMING SYSTEM, METHOD OF MAKING AND USE THEREOF

(75) Inventors: Shalaby W. Shalaby, Anderson, SC (US); Joel Corbett, Anderson, SC (US); Jason Olbrich, Clemson, SC (US); Joanne E. Shalaby, legal representative, Anderson, SC (US)

(73) Assignee: Poly-Med, Inc., Anderson, SC (US)

(*) Notice: Subject to any disclaimer, the term of this patent is extended or adjusted under 35 U.S.C. 154(b) by 74 days.

(21) Appl. No.: 13/274,824

(22) Filed: Oct. 17, 2011

(65) Prior Publication Data
US 2013/0095087 A1   Apr. 18, 2013

(51) Int. Cl.
| | | |
|---|---|---|
| *A61K 45/00* | (2006.01) | |
| *A61K 47/22* | (2006.01) | |
| *A61K 38/39* | (2006.01) | |
| *A61K 47/08* | (2006.01) | |
| *A61K 47/20* | (2006.01) | |
| *A61K 31/08* | (2006.01) | |
| *A61K 45/06* | (2006.01) | |
| *A61K 47/34* | (2006.01) | |
| *A61K 35/14* | (2006.01) | |
| *A61K 31/65* | (2006.01) | |
| *A61K 38/48* | (2006.01) | |
| *A61K 38/36* | (2006.01) | |

(52) U.S. Cl.
CPC .............. *A61K 31/08* (2013.01); *A61K 47/22* (2013.01); *A61K 38/39* (2013.01); *A61K 47/08* (2013.01); *A61K 47/20* (2013.01); *A61K 45/06* (2013.01); *A61K 47/34* (2013.01); *A61K 35/14* (2013.01); *A61K 31/65* (2013.01); *A61K 38/4833* (2013.01); *A61K 38/36* (2013.01)
USPC ....................................................... 424/93.72

(58) Field of Classification Search
USPC ........................................................ 424/93.72
See application file for complete search history.

(56) References Cited

U.S. PATENT DOCUMENTS

| | | | | |
|---|---|---|---|---|
| 5,320,624 | A | * | 6/1994 | Kaplan et al. ................... 606/77 |
| 5,612,052 | A | | 3/1997 | Shalaby |
| 5,714,159 | A | | 2/1998 | Shalaby |
| 6,413,539 | B1 | | 7/2002 | Shalaby |
| 6,531,111 | B1 | | 3/2003 | Whalen, II et al. |
| 7,649,023 | B2 | | 1/2010 | Shih et al. |
| 2002/0151650 | A1 | | 10/2002 | Pathak et al. |
| 2004/0225077 | A1 | * | 11/2004 | Gravett et al. ................ 525/418 |
| 2005/0255091 | A1 | | 11/2005 | Loomis |

(Continued)

FOREIGN PATENT DOCUMENTS

WO   WO/2010068381   *   6/2010  .............. A61L 31/06

OTHER PUBLICATIONS

Malik et al., Atrigel: A potential parenteral controlled drug delivery system, Der Pharmacia Sinica, 2010, 1(1): pp. 74-81.*
Bajpai et al., Responsive polymers in controlled drug delivery, Progress in Polymer Science 33(2008) pp. 1088-1118.*
Ruel-Gariepy et al., In situ-forming hydrogels—review of temperature-sensitive systems, European Journal of Pharmaceutics and Biopharmaceutics 58 (2004) pp. 409-426.*

(Continued)

*Primary Examiner* — Larry Riggs
*Assistant Examiner* — Karla Dines

(57) ABSTRACT

An in situ gel-forming composition is disclosed. The in situ gel-forming composition comprises one or more absorbable polymers, solvents such as N-methyl-2-pyrrolidone, polyethylene glycol or DMSO, and optionally one or more bioactive agent. The composition forms a hydrogel or semi-solid mass on contact with an aqueous environment. The method of using in situ gel-forming composition for various applications is also disclosed.

9 Claims, 1 Drawing Sheet

(56) References Cited

U.S. PATENT DOCUMENTS

| | | |
|---|---|---|
| 2006/0069168 A1* | 3/2006 | Tabata et al. ............... 514/772.1 |
| 2009/0202467 A1* | 8/2009 | Bock ......................... 424/78.38 |
| 2009/0233887 A1 | 9/2009 | Shalaby et al. |
| 2009/0291925 A1 | 11/2009 | Shalaby |
| 2010/0056646 A1 | 3/2010 | Shalaby et al. |
| 2010/0255016 A1 | 10/2010 | Shalaby et al. |

OTHER PUBLICATIONS

V and P Scientific Viscosity Table, one page.*
The International Search Report and Written Opinion of the International Searching Authority, mailed Jul. 10, 2012 (Application No. PCT/US2011/056537, filed Oct. 17, 2011).

* cited by examiner

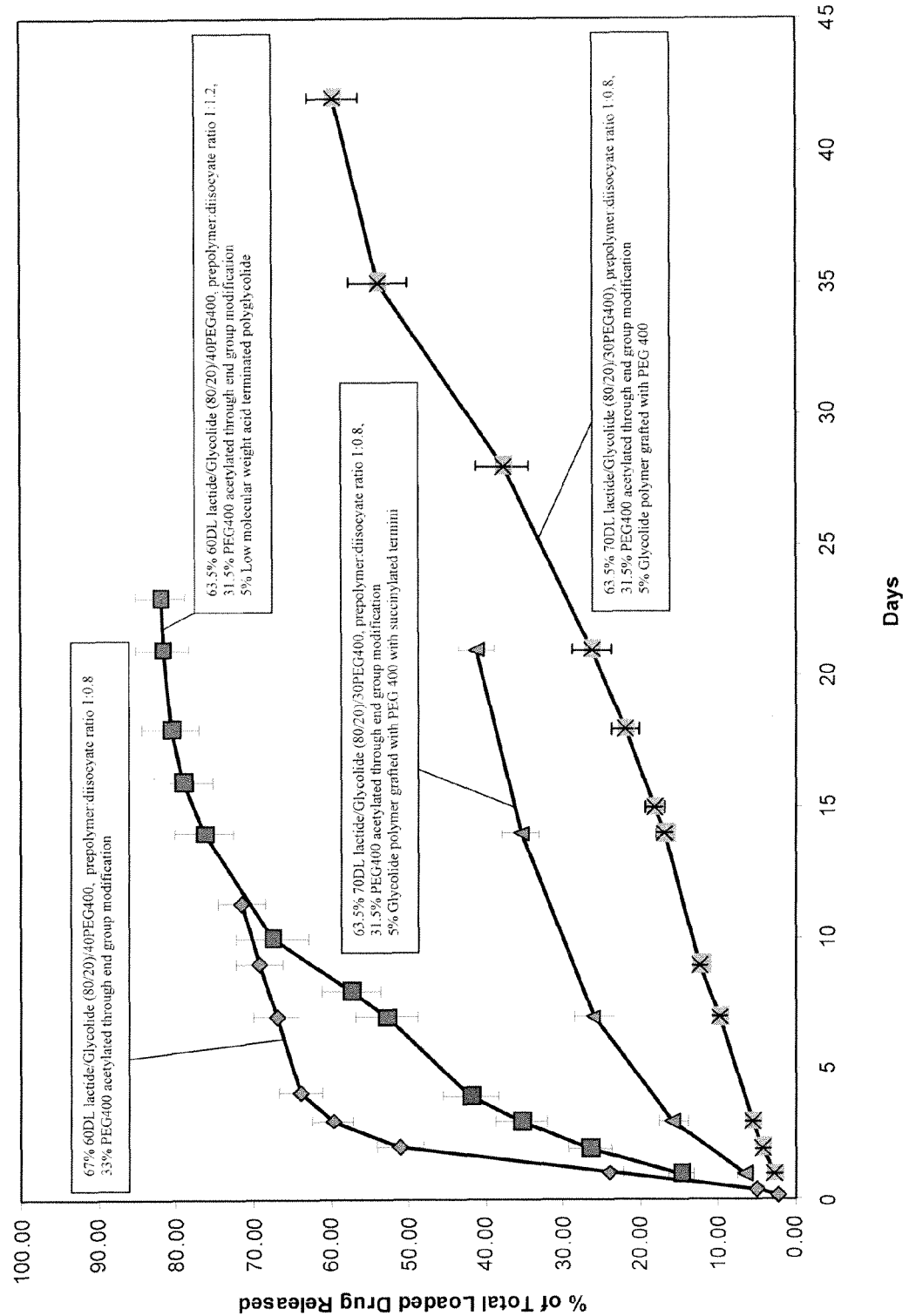

ABSORBABLE IN SITU GEL-FORMING SYSTEM, METHOD OF MAKING AND USE THEREOF

FIELD

This application relates generally to an absorbable gel system and, in particular, to an in situ gel-forming system for various applications, such as vascular applications.

BACKGROUND

Vascular disease, such as coronary and peripheral artery diseases, aneurysms, and peripheral venous diseases, as well as vascular conditions caused by medical procedures such as angioplasty and stenting, often require localized treatment. In situ gel-forming systems provide an ideal platform for the treatment of vascular diseases and conditions. Biodegradable polymers, such as polyester copolymers, have been used in gel-forming systems since they present tunable chemical properties, excellent mechanical properties, and good blood compatibility. These polymer compositions, however, are often too viscose to be delivered effectively through a needle or catheter and, therefore, have limited use in vascular applications where delivery through a needle or a catheter is required. Accordingly, there exists a need for an in situ gel-forming system that can be easily delivered through small-gauge needles or catheters.

SUMMARY

One aspect of the present invention relates to an in situ gel-forming composition. The composition comprises one or more absorbable polymers and a solvent selected from the group consisting of N-methyl-2-pyrrolidone (NMP), polyethylene glycol (PEG), dimethyl sulfoxide (DMSO) and mixtures thereof, wherein the composition has a viscosity in the range of about 1 cP to about 100 cP and forms a hydrogel or semi-solid mass on contact with an aqueous environment.

Another aspect of the present invention relates to a method for treating a vascular disease or condition in a subject. The method comprises injecting into the subject, at a treatment site, an effective amount of an in situ gel-forming composition. The composition comprises one or more absorbable polymers and a solvent selected from the group consisting of N-methyl-2-pyrrolidone (NMP), polyethylene glycol (PEG), dimethyl sulfoxide (DMSO) and mixtures thereof, wherein the composition has a viscosity in the range of about 1 cP to about 100 cP and forms a hydrogel or semi-solid mass on contact with an aqueous environment. In certain embodiments, the vascular disease is a peripheral venous disease selected from spider veins, spider telangiectasias, reticular veins, reticular varicosities, venulectasias, tributary varicose veins, bulging varicose veins, vein tributaries, varicose saphenous veins, or combinations thereof. In other embodiments, the vascular disease or condition is a disease or condition selected from the group consisting of coronary and peripheral artery diseases, aneurysms, and peripheral venous diseases, and vascular conditions caused by angioplasty or stenting.

Another aspect of the present invention relates to method for treating a cancer or tumor in a subject. The method comprises injecting into the subject an effective amount of an in situ gel-forming composition. The composition comprises one or more absorbable polymers, a solvent selected from the group consisting of N-methyl-2-pyrrolidone (NMP), polyethylene glycol (PEG), dimethyl sulfoxide (DMSO) and mixtures thereof, and one or more chemotherapy agents, wherein the composition has a viscosity in the range of about 1 cP to about 100 cP and forms a hydrogel or semi-solid mass on contact with an aqueous environment.

Another aspect of the present invention relates to method for controlling bleeding in a subject during an embolization procedure. The method comprises injecting into the subject, at a treatment site, an effective amount of an in situ gel-forming composition. The composition comprises one or more absorbable polymers, a solvent selected from the group consisting of N-methyl-2-pyrrolidone (NMP), polyethylene glycol (PEG), dimethyl sulfoxide (DMSO) and mixtures thereof, and one or more bioactive agents selected from the group consisting of: collagen, thrombin, activated platelets, chitosan, antifibrinolytics, vitamin K, fibrinogen, and blood coagulation factors, wherein the composition has a viscosity in the range of about 1 cP to about 100 cP and forms a hydrogel or semi-solid mass on contact with an aqueous environment.

Another aspect of the present invention relates to a method for minimizing re-stenosis following angioplasty. The method comprises administering at a site of angioplasty, an effective amount of an in situ gel-forming composition. The composition comprises one or more absorbable polymers, a solvent selected from the group consisting of N-methyl-2-pyrrolidone (NMP), polyethylene glycol (PEG), dimethyl sulfoxide (DMSO) and mixtures thereof, and one or more bioactive agents that inhibits neoplastic growth, wherein the composition has a viscosity in the range of about 1 cP to about 100 cP and forms a hydrogel or semi-solid mass on contact with an aqueous environment.

Another aspect of the present invention relates to a method for endovascular repair of aneurysms to prevent type I and type II leaks. The method comprises administering at a site of aneurysm, an effective amount of an in situ gel-forming composition. The composition comprises one or more absorbable polymers, a solvent selected from the group consisting of N-methyl-2-pyrrolidone (NMP), polyethylene glycol (PEG), dimethyl sulfoxide (DMSO) and mixtures thereof, and one or more agents suitable for endovascular repair of aneurysms, wherein the composition has a viscosity in the range of about 1 cP to about 100 cP and forms a hydrogel or semi-solid mass on contact with an aqueous environment.

Another aspect of the present invention relates to a kit comprising the in situ gel-forming composition of the present invention and instructions about how to use the in situ gel-forming composition. In one embodiment, the kit comprises the in situ gel-forming composition packaged in a pre-filled syringe or vial.

BRIEF DESCRIPTION OF DRAWINGS

FIG. 1 is a diagram showing release curves of several bioactive formulations using polyurethane compositions.

DETAILED DESCRIPTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention.

In case of conflict, the present specification, including definitions, will control. Following long-standing patent law convention, the terms "a", "an" and "the" mean "one or more" when used in this application, including in the claims.

The term "effective amount" denotes the amount of a medicament or of a pharmaceutical active ingredient which causes a biological or medical response in a tissue, system, animal or human which is sought or desired, for example, by a researcher or physician. In addition, the term "effective amount" denotes an amount which, compared with a corresponding subject who has not taken this amount, has the following consequence: improved treatment, healing, prevention or elimination of a disease, condition, syndrome, disease state, complaint, disorder or prevention of side effects or also the reduction in the progress of a disease, complaint or disorder. The term "effective amount" also encompasses the amounts which are effective for increasing normal physiological function.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

In Situ Gel-forming Composition

One aspect of the present invention relates to an injectable gel-forming composition that comprises one or more absorbable polymers, a solvent such as NMP, polyethylene glycol, DMSO, and optionally one or more bioactive agents. The composition is injectable and forms a hydrogel or semi-solid mass on contact with an aqueous environment at the treatment site. The composition can be used for the treatment of (1) various vascular diseases, such as coronary and peripheral artery diseases, aneurysms and peripheral venous diseases, (2) vascular conditions caused by medical procedures, such as angioplasty and stenting, and (3) other applications such as localized cancer treatment.

Absorbable Polymers

The one or more absorbable polymers can be any absorbable polyester/polyether copolymer or mixture of polyester/polyether copolymers that is miscible with a solvent such as NMP, polyethylene glycol or DMSO and is capable of forming a hydrogel or semi-solid mass on contact with an aqueous environment.

As used herein, the term "absorbable polymer" or "biodegradable polymer" refers to a polyester copolymer that can be broken down by either chemical or physical process, upon interaction with the physiological environment at the implantation site, and erodes or dissolves within a period of time, e.g., within days, weeks or months. An absorbable or biodegradable polymer serves a temporary function in the body, such as closing a varicose vein, supporting or seal a lumen or delivering a drug, and is then degraded or broken into components that are metabolizable or excretable.

The one or more absorbable polymers can be in linear or branched form. In certain embodiments, the one or more absorbable polymers comprise a molecular chain having a hydrophilic block, designated "Y" herein, and a relatively hydrophobic polyester block, designated "X" herein. Hydrophobic block X and hydrophilic block Y more preferably comprises a molecular structure having the following formula: X—Y—X or $(X—Y)_n$, and branched structures thereof. Most preferably, hydrophobic block X comprises a polyester formed by grafting a glycolide, lactide, ε-caprolactone, p-dioxanone, trimethylene carbonate or combinations thereof, onto the hydroxylic or amino groups of a hydrophilic polymer precursor i.e., Y; hydrophilic block Y comprises a polyoxyethylene, poly(oxyethylene-b-oxypropylene), polypeptide polyalkylene oxamate, a polysaccharide, and derivatives thereof; or a liquid, high molecular weight polyether glycol interlinked with an oxalate or succinate functionalities in linear or branched form.

The term "Hydrophobic Block(s)" as used herein, refers to absorbable polyester chain block(s) or segment(s) of variable length which, is present in an isolated form, will produce practically amorphous (with less than 5% crystallinity) or totally amorphous material having a $T_g$ of less than 25° C., and preferably, is a viscous liquid at room temperature. Hydrophobic block(s) X comprises copolymeric segments of known chemistries in the art, such as, those comprised from cyclic lactones (e.g., glycolide, l-lactide, dl-lactide, ε-caprolactone, p-dioxanone, trimethylene carbonate), polyalkylene oxalate, and the like. More preferably, hydrophobic segment(s) or block(s) X comprises lactide/glycolide copolymer (with 51 to 80% l- or dl-lactide).

The term "Hydrophilic Block(s)" as used herein, refers to polymeric blocks or segments which, if present in an isolated form, will be water soluble. Hydrophilic block(s) or segment(s) Y comprises poly(oxyethylene), with or without a minor component of a higher homolog, such as, poly(oxypropylene)-polypeptide, polyalkylene oxamate, a polysaccharide, or derivatives thereof. The length of the hydrophilic block and its weight fractions can be varied to modulate the rate of gel formation, its modulus, its water content, diffusivity of bioactive drug through it, its adhesiveness to surrounding tissue, and bioabsorbability.

The term "hydrogel" or "hydrogel mass" as used herein, refers to materials which have a high tendency for water absorption and/or retention, and maintain mechanical integrity through physical crosslinks which are reversible in nature.

The term "semi-solid" or "semi-solid mass" as used herein, refers to a material which is similar to a solid in some respects (e.g., it can support its own weight and hold its shape), but also shares some properties of liquids, such as shape conformity to something applying pressure to it, or the ability to flow under pressure.

In other embodiments, the one or more absorbable polymers optionally comprise carboxylic end-groups formed by any known technique in the art, such as, for example, end-group succinylation and end-group acetylation. This facilitates ionically binding a biologically active agent or drug to the absorbable polymer such that the drug release can be modulated. The biologically active agent or drug is preferably present on the absorbable polymer in an insoluble form, such as, (1) a microparticulate dispersion, (2) a surface-deposited coating onto an absorbable microporous microparticles, and/or (3) ionically bound molecules onto the surfaces of absorbable microporous microparticles.

In certain other embodiments, the one or more absorbable polymers comprise a segmented, aliphatic polyurethane comprising polyoxyalkylene glycol chains covalently linked to polyester or polyester-carbonate chain segments, interlinked with aliphatic urethane segments. The polyoxyalkylene glycol chains comprise at least one type of oxyalkylene sequences selected from the group represented by oxyethylene, oxypropylene, oxytrimethylene, and oxytetramethylene repeat units. In certain embodiments, the polyoxyalkylene glycol chain has an average molecular weight of 200-1200 dalton. In other embodiments, the polyoxyalkylene glycol chain is PEG 200, PEG 300, PEG 400, PEG 500, PEG 600, PEG 700, PEG 800, PEG 900, PEG 1000, and derivatives thereof. The polyester or polyester-carbonate chain segments are derived from at least one cyclic monomer selected from the group represented by ε-caprolactone, trimethylene carbonate, p-dioxanone, 1,5-dioxepan-2-one, l-lactide, dl-lactide, glycolide, morpholinedione, and combinations thereof. The aliphatic urethane segments are derived from at least one diisocyanate selected from the group consisting of hexamethylene diisocyanate, lysine-derived diisocyanate, and cyclohexane bis(methylene isocyanate).

In certain embodiments, the segmented, aliphatic polyurethane has an ether/ester mass ratios of 20-49/80-51, preferably 25-40/75-55 and, most preferably 30-40/70-60. In other embodiments, the segmented, aliphatic polyurethane has a prepolymer/diisocyante mass ratio in the range of 1:0.5 to 1:1.4. In one embodiment, the segmented, aliphatic polyurethane has a prepolymer/diisocyante mass ratio of 1:0.66, 1:0.8 or 1:1.2.

In other embodiments, the one or more absorbable polymers comprise a relatively slow-absorbing, segmented polyether-carbonate-urethanes (PECU), which possesses one or more of the following features: (a) exhibits <20 percent or no solubility in water; (b) is made to be liquids at about 50° C.; (c) has a weight average molecular weight exceeding 10 kDa; (d) swells in an aqueous environment leading to an increase of volume of at least 3 percent, and (e) is miscible in solvents such as NMP, polyethylene glycol or DMSO, to facilitate their use as injectable formulations that undergo gel-formation when introduced to aqueous biological sites.

In other embodiments, the one or more absorbable polymers comprise relatively fast-absorbing segmented aliphatic polyether-ester urethanes (PEEU) and polyether-carbonate-ester urethanes (PECEU). In one embodiment, the relatively fast-absorbing segmented aliphatic PEEU and PECEU possess one or more of the following features: (a) exhibit limited (<20 percent) or no solubility in water; (b) are made to be liquids at about 50° C.; (c) have a weight average molecular weight exceeding 10 kDa; (d) swell in an aqueous environment leading to an increase of volume of at least 3 percent; and (e) are miscible in a solvent such as NMP, polyethylene glycol or DMSO, to facilitate their use as injectable formulations that undergo gel-formation when introduced to aqueous biological sites.

In yet other embodiments, the one or more absorbable polymers comprise segmented, aliphatic polyether-ester urethanes (APEEU) and polyether-ester-carbonate urethanes (APEECU). Typical APEEUs and APEECUs comprise polyoxyalkylene chains (such as those derived from polyethylene glycol and block or random copolymers of ethylene oxide and propylene oxide) covalently linked to polyester or polyester-carbonate segments (derived from at least one monomer selected from the group represented by trimethylene carbonate, c-caprolactone, lactide, glycolide, p-dioxanone, 1,5-dioxepan-2-one, and a morpholinedione) and interlinked with aliphatic urethane segments derived from 1,6 hexamethylene-, 1-4 cyclohexane-, cyclohexane-bis-methylene-, 1,8 octamethylene- or lysine-derived diisocyanate.

In other embodiments, the absorbable polymers comprise absorbable polyester copolymers or mixtures thereof. Suitable absorbable polyester copolymers include, but are not limited to, lactide/glycolide copolymers, caprolactone/glycolide copolymers, lactide/trimethylene carbonate copolymers, lactide/glycolide/caprolactone tripolymers, lactide/glycolide/trimethylene carbonate tripolymers, lactide/caprolactone/trimethylene carbonate tripolymers, glycolide/caprolactone/trimethylene carbonate tripolymers, and lactide/glycolide/caprolactone/trimethylene carbonate terpolymers.

In certain embodiments, the polyester copolymer comprise a lactide/glycolide copolymer with a lactide/glycolide mole ratio of 60-90/40-10.

Solvent

The gel-forming polymer is dissolved in a solvent to form an injectable liquid formulation. Suitable solvents include, but are not limited to, NMP, polyethylene glycols such as PEG 400 and PEG 200, DMSO, methyl acetate, ethyl acetate, ethanol, and caprolactone monomer.

The Polymer-To-Solvent Ratio

The polymer-to-solvent ratio can be modulated in concert with the bioactive agent solubility, its intended release site, and preferred gelation rate and release rate. In one embodiment, the polymer-to-solvent (w/w) ratio is in the range of about 5:95 to 55:45, preferably in the range of about 20:80 to 50:50 w/w. In certain embodiments, the solvent comprises NMP and the polymer-to-solvent (w/w) ratio is in the range of 10:90 to 50:50, 10:90 to 20:80, or 15:85 to 30:70. In other embodiments, the solvent comprises PEG and the polymer-to-solvent (w/w) ratio is in the range of 50:50 to 70:30. In other embodiments, the solvent comprises methyl acetate and/or ethyl acetate, and the polymer-to-solvent (w/w) ratio is in the range of 10:90 to 50:50. In other embodiments, the solvent comprises caprolactone monomer and the polymer-to-solvent (w/w) ratio is in the range of 40:60 to 60:40. In yet other embodiments, the solvent comprises DMSO and the polymer-to-solvent (w/w) ratio is in the range of 70:30 to 90:10.

Bioactive Agents

The injectable gel-forming composition may be used as vehicles for the controlled release of one or more bioactive agents. Examples of such bioactive agents includes, but are not limited to, antifungal agents, antibacterial agents and antibiotics, anti-inflammatory agents, immunosuppressive agents, immunostimulatory agents, antiseptics, anesthetics, nutritional agents, antioxidants, lipopolysaccharide complexing agents, peroxides, cell/tissue growth factors, antineoplastic and anticancer agents.

Examples of antifungal agents include, but are not limited to, polyene antifungals, azole antifungal drugs, and Echinocandins.

Examples of antibacterial agents and antibiotics include, but are not limited to, erythromycin, penicillins, cephalosporins, doxycycline, gentamicin, vancomycin, tobramycin, clindamycin, and mitomycin.

Examples of anti-inflammatory agents include, but are not limited to, non-steriodal anti-inflammatory drugs such as ketorolac, naproxen, diclofenac sodium and fluribprofen.

Examples of immunosuppressive agents include, but are not limited to, glucocorticoids, alkylating agents, antimetabolites, and drugs acting on immunophilins such as ciclosporin and tacrolimus.

Examples of immunostimulatory agents include, but are not limited to, antibodies, TNFα, VEGF, interleukins, interferon, cytokines, toll-like receptor (TLR) agonists, cytokine receptor agonist, CD40 agonist, Fc receptor agonist, CpG-containing immunostimulatory nucleic acid, complement receptor agonist, or an adjuvant.

Examples of antiseptics include, but are not limited to, chlorhexidine and tibezonium iodide.

Examples of anesthetic include, but are not limited to, lidocaine, mepivacaine, pyrrocaine, bupivacaine, prilocaine, and etidocaine.

Examples of antioxidants include, but are not limited to, antioxidant vitamins, carotenoids, and flavonoids.

Examples of lipopolysaccharide complexing agents include, but are not limited to, polymyxin.

Examples of peroxides, include, but are not limited to, benzoyl peroxide and hydrogen peroxide.

Examples of cell growth promoting factors include, but are not limited to, epidermal growth factors, human platelet derived TGF-β, endothelial cell growth factors, thymocyte-activating factors, platelet derived growth factors, fibroblast growth factor, fibronectin or laminin.

Examples of antineoplastic/anti-cancer agents include, but are not limited to, paclitaxel, carboplatin, miconazole, leflunamide, and ciprofloxacin.

It is recognized that in certain forms of therapy, combinations of agents/drugs in the same delivery system i.e., the in situ gel-forming system of the present invention, can be useful in order to obtain an optimal effect. Thus, for example, an antibacterial and an anti-inflammatory agent may be combined in a single copolymer to provide combined effectiveness.

In certain embodiments, the in situ gel-forming composition further comprises a sclerosant for the treatment of varicose vein. In some embodiments, the sclerosant comprises polidocanol, sodium tetradecyl sulfate, or both. In other embodiments, the in situ gel-forming composition comprises polidocanol in the amount of from 0.2% to 5.0% (w/w), 0.2% to 1.0% (w/w), 0.5% to 1.5% (w/w), 0.5% to 2.5% (w/w), 1.0% to 2.0% (w/w), 2.0% to 3.0% (w/w), 3.0% to 4.0% (w/w) and 4.0% to 5.0% (w/w). In related embodiments, the composition further comprises a vasoconstrictor. Examples of vasoconstrictor include, but are not limited to, 3-(4,5-dihydro-1H-imidazol-2-ylmethyl)-2,4-dimethyl-6-tert-butyl-phenol (hereinafter, "oxymetazoline"), epinephrine, norepinephrine, levophed, or dopamine. In some embodiments, the vasoconstrictor is oxymetazoline. In other embodiments, the vasoconstrictor is a long acting vasoconstrictor that is effective for at least 8 hours, 10 hours, or 12 hours after administration. In yet other related embodiments, the composition comprises both a sclerosant and a vasoconstrictor.

Solid Absorbable Carrier

In some embodiments, the in situ gel-forming composition further comprises a solid absorbable carrier to carry the one or more bioactive agent. The bioactive agent/drug can be deposited, wholly or in part, on the solid absorbable carrier. In certain embodiments, the solid absorbable carrier is an absorbable, microporous low molecular weight polyester which is highly crystalline and practically insoluble in the absorbable polymer of the in situ gel-forming composition.

In one embodiment, the in situ gel-forming composition comprises the solid carrier and the absorbable polymer at a weight ratio of 20/80, with the carrier being a low molecular, microporous polyglycolide with 0.70 to 0.95 solid fraction, average particle size of 0.5-200 micron and carboxyl-bearing chains. High concentration of carboxylic groups on the chains can be achieved by preparing the solid carrier using di- or poly-carboxylic acid as initiators. The deposited agent on the solid carrier can exhibit a release profile which can be multiphasic, including: (a) simple, fast diffusion of soluble free drug through the in situ hydrogel; (b) slow diffusion of soluble free drug housed in the pores of the solid carrier; and, (c) drug release at the surface (both exterior and pore) of the solid carrier or the chain ends of carboxylated A chains by ion exchange of ionically bound molecules. By varying the concentration of the solid carrier in the in situ gel-forming composition, the flow characteristics and release profile of the agent can be modulated.

In a certain embodiment, the absorbable carrier comprises microspheres or nanoparticles, such as biodegradable polylactic acid (PLA) microspheres, for controlled drug delivery. Other suitable biodegradable polymers include, but are not limited to, polyglycolic acid (PGA), lactic acid-glycolic acid copolymer (PLGA), poly-ϵ-caprolactone (PCL), lactic acid-ϵ-caprolactone copolymer (PLCL), polydioxanone (PDO), polytrimethylene carbonate (PTMC), poly(amino acid), polyanhydride, polyorthoester and copolymers thereof. The microspheres or nanoparticles can be prepared by polymerizing the monomeric mixture under polymerization conditions in the presence of one or more bioactive agents such that the bioactive agent(s) is entrapped in the polymerization product.

Other Components

The injectable gel-forming composition may further comprise other components such as stabilizers against premature polymerization (e.g., hydroxyquinone or butylated hydroxyanisole) and buffering agents to maintain desired pH.

Viscosity

In certain embodiments, the in situ gel-forming composition of the present invention is in a liquid or semi-liquid form at 37° C., preferably, at 25° C. or room temperature. In certain embodiments, the in situ gel-forming composition is in a liquid at room temperature that can be easily administered through a syringe needle or a catheter that is standard/typical for current sclerotherapy procedures.

In some embodiments, in situ gel-forming composition is an injectable liquid at room temperature. As used hereinafter, the term "injectable liquid" refers to a liquid that can be administered into a recipient through an injection device commonly used in medical art, such as needles, syringes and catheters. In certain embodiments, the injectable liquid has viscosity that allows the liquid to be administered through a 10 gauge needle without excessive force. In other embodiments, the injectable liquid has a viscosity that allows the liquid to be administered through a 30 gauge needle without excessive force. In certain embodiments, the injectable liquid has a viscosity in the range of about 1 cP (centiPoise) to about 1000 cP, about 1 cP to about 300 cP, about 1 cP to about 100 cP, about 1 cP to about 30 cP, about 10 cP to about 300 cP, about 10 cP to about 100 cP, about 30 cP to about 300 cP and about 30 cP to about 100 cP.

Rate of Gelation and Rate of Absorption

The in situ gel-forming composition of the present invention is formulated for rapid gelation at the treatment site. In certain embodiments, the in situ gel-forming composition is capable of forming a hydrogel or semi-solid mass at a treatment site in a period of 1-120 seconds, 1-5 minutes, 5-15 minutes, or 15-30 minutes. In certain embodiments, the in situ gel-forming composition forms a hydrogel or semi-solid mass at a treatment site within 15 seconds, 30 seconds, 60 seconds or 90 seconds. In certain embodiments, the gelation time is determined visually by observing the period between injection and formation of the solid mass. Upon exposure to an aqueous environment, the diluent/solvent portion of the solution precipitates leaving the hardened polymeric hydrogel or semi-solid mass that can be visually detected. The rate of gelation may be adjusted by adding one or more gelation accelerators to the in situ gel-forming composition. Compounds that may serve as gelation accelerators include, but are not limited to, collagen, thrombin, activated platelets, chitosan, fibrinogen and antifibrinolytics.

In other embodiments, the in situ gel-forming composition of the present invention is formulated for slow degradation at the treatment site. In some embodiments, the in situ gel-forming composition of the present invention is formulated for a degradation time of 1-3 weeks, 1-3 months, 3-6 months, or 6-12 months through utilization of different polymer configurations.

The in situ gel-forming composition can be formulated for various vascular applications. In some embodiments, the in situ gel-forming composition comprises a sclerosant and is formulated for sclerotherapy of venous obliteration. In other embodiments, the in situ gel-forming composition comprises collagen, thrombin, activated platelets, chitosan, fibrinogen or antifibrinolytics and is formulated for use in embolization procedures to control bleeding. In other embodiments, the in situ gel-forming composition comprises a chemotherapy agent and is formulated for chemo-embolization procedures for localized cancer therapy. In other embodiments, the in situ gel-forming composition comprises paclitaxel, sirolimus zotarolimus or rapamycin and is formulated for localized release of drug to minimize re-stenosis after angioplasty. In yet other embodiments, the in situ gel-forming composition comprises one or more bioactive agents suitable for endovascular repair of aneurysms to prevent type I and type II leaks, and is formulated as an adjunct to endovascular repair of aneurysms to prevent type I and type II leaks. Examples of bioactive agents suitable for endovascular repair of aneurysms include, but are not limited to, collagen, thrombin, activated platelets, chitosan, fibrinogen or antifibrinolytics.

Treatment Methods

Another aspect of the present invention relates to methods for treating various diseases and conditions using the in situ gel-forming composition of the present invention. The method comprises the steps of injecting into a subject in need of such treatment an effective amount of an in situ gel-forming composition comprising one or more absorbable polymers, a solvent such as N-methyl-2-pyrrolidone (NMP), polyethylene glycol or DMSO, and optionally one or more bioactive agents, wherein said in situ gel-forming composition forms a hydrogel or semi-solid mass on contact with an aqueous environment at a treatment site.

In some embodiments, the method relates to treatment of a vascular disease or condition. Examples of the vascular diseases and conditions include, but are not limited to, coronary and peripheral artery diseases, aneurysms, and peripheral venous diseases, as well as vascular conditions caused by medical procedures such as angioplasty and stenting. In another embodiment, the method relates to treatment for peripheral venous diseases such as spider veins, spider telangiectasias, reticular veins, reticular varicosities, venulectasias, tributary varicose veins, bulging varicose veins, vein tributaries, varicose saphenous veins, or combinations thereof. The treatment prevents or ameliorates symptoms associated with varicose vein disease, such as edema, skin changes, ulcers, sequelae of varicose veins, bruising, staining, thrombus formation, trapped blood, blood clots, or combinations thereof. Preferably, the symptoms are prevented or ameliorated without use of compression stockings.

In other embodiments, the method relates to treatment of venous malformations, arteriovenous malformations, Klippel-Trenaunay Syndrome, aneurysms, endoleaks after aneurysm repair, cerebral aneurysms, tumors, acute bleeding (from trauma), cancer, or combinations thereof.

In other embodiments, the method relates to treatment of cancer or tumor using an in situ gel-forming composition that comprises a chemotherapy agent.

Examples of cancer include, but are not limited to, lung cancer, cancer of the peritoneum, hepatocellular cancer, gastric or stomach cancer including gastrointestinal cancer, pancreatic cancer, glioblastoma, cervical cancer, ovarian cancer, liver, cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, brain, and associated metastases.

In other embodiments, the present invention relates to a method for controlling bleeding during an embolization procedure. The method comprises the step of administering at a site of embolization, an effective amount of an in situ gel-forming composition comprising one or more absorbable polymers, a solvent such as NMP, polyethylene glycol or DMSO, and one or more bioactive agents, wherein said in situ gel-forming composition forms a hydrogel or semi-solid mass on contact with an aqueous environment at a treatment site. Suitable bioactive agents include, but are not limited to, collagen, thrombin, activated platelets, chitosan, antifibrinolytics, vitamin K, fibrinogen, and blood coagulation factors.

In other embodiments, the present invention relates to a method for minimizing re-stenosis following angioplasty. The method comprises the step of administering at a site of angioplasty, an effective amount of an in situ gel-forming composition comprising one or more absorbable polymers, a solvent such as N-methyl-2-pyrrolidone (NMP), polyethylene glycol or DMSO, and one or more bioactive agents, wherein said in situ gel-forming composition forms a hydrogel or semi-solid mass on contact with an aqueous environment at a treatment site. Suitable bioactive agents include, but are not limited to, paclitaxel, sirolimus zotarolimus and rapamycin.

In yet other embodiments, the present invention relates to a method for endovascular repair of aneurysms to prevent type I and type II leaks. The method comprises the step of administering at a site of aneurysm, an effective amount of an in situ gel-forming composition comprising one or more absorbable polymers, a solvent such as NMP, polyethylene glycol or DMSO, and one or more bioactive agents suitable for endovascular repair of aneurysms, wherein said in situ gel-forming composition forms a hydrogel or semi-solid mass on contact with an aqueous environment at a treatment site. Bioactive agents suitable for endovascular repair of aneurysms include, but are not limited to, collagen, thrombin, activated platelets, chitosan, fibrinogen or antifibrinolytics.

Another aspect of the present invention relates to a method for drug delivery. The method comprises the step of administering into a subject, an effective amount of an in situ gel-forming composition comprising one or more absorbable polymers, a solvent such as NMP, polyethylene glycol or DMSO, and biodegradable microspheres or nanoparticles comprising one or more bioactive agents, wherein said in situ gel-forming composition forms a hydrogel or semi-solid mass on contact with an aqueous environment at a treatment site.

Kits

Another embodiment of the present invention is directed to a kit comprising the in situ gel-forming composition of the present invention and instructions about how to use the in situ gel-forming composition. In one embodiment, the kit comprises the in situ gel-forming composition packaged in a pre-filled syringe or vial.

The present invention is further illustrated by the following examples which should not be construed as limiting. The contents of all references, patents and published patent applications cited throughout this application, as well as the Figures are incorporated herein by reference.

EXAMPLE 1

Synthesis and Characterization of Polyether-Ester Urethane: General Method

For an initial charge, poly(ethylene glycol) ($M_n$=400 Da) and tin(II) 2-ethyl hexanoate was added to a 500 mL, 3-neck, round-bottom flask equipped with a PTFE coated magnetic stir bar. The contents were heated to 70° C. and allowed to stir for 10 minutes. For a second charge, dl-lactide and glycolide were added and the contents were heated to 135° C. Conditions were maintained until practically complete monomer conversion was achieved. The magnetic stir bar was removed and replaced with a stainless steel mechanical stirrer. The polymer was cooled to room temperature. For a third charge, 1,6-diisocyanatohexane was added and the contents were stirred until complete mixing was achieved. The contents were stirred and heated to 100° C. Conditions were maintained for 1.25 hours. The polymer was allowed to cool to room temperature and then dissolved in an equal part of tetrahydrofuran. The polymer solution was treated with 5 mL of 2-propanol at 55° C., then precipitated in cold water. The purified polymer was dried to a constant weight at 55° C. on a rotary evaporator. The purified polymer was characterized for molecular weight by GPC using tetrahydrofuran as the mobile phase. Identity and composition were confirmed by FT-IR and NMR, respectively.

EXAMPLE 2

Preparation and Evaluation of Bioactive Formulations Using Polyurethane Composition Obtained From Example 1: General Method An aliquot of the product of Example 1 (4.5 g) was heated to 50° C. then mixed thoroughly at that temperature with polyethylene glycol (PEG-400) having a molecular weight of 400 Da (4.4 g). The mixed polymers were allowed to reach room temperature and then thoroughly mixed with a second aliquot of PEG-400 (1.1 g) premixed with the drug solution in ethanol. The final formulation was dried under reduced pressure to distill the ethanol prior to conducting the drug release study. The release profile of the specific drug in the respective formulation was conducted using buffered solution and HPLC. FIG. 1 shows exemplary release curves of doxycycline from several test formulations.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following embodiments. The embodiments are intended to cover the components and steps in any sequence which is effective to meet the objectives there intended, unless the context specifically indicates the contrary. Moreover, Applicant hereby discloses all subranges of all ranges disclosed herein. These subranges are also useful in carrying out the present invention.

What is claimed is:

1. An in situ gel-forming composition, comprising:
   one or more absorbable polymer(s) comprising a multi-block copolymer containing blocks of poly(lactide-co-trimethylene carbonate) and blocks of poly(lactide-co-glycolide); and
   a solvent selected from the group consisting of N-methyl-2-pyrrolidone (NMP), polyethylene glycol (PEG), dimethyl sulfoxide (DMSO) and mixtures thereof,
   wherein said composition has a viscosity in the range of about 1 cP to about 100 cP, and is a free flowing injectable liquid, and forms a hydrogel or semi-solid mass on contact with an aqueous environment.

2. The in situ gel-forming composition of claim 1, further comprising one or more bioactive agent(s).

3. The in situ gel-forming composition of claim 1, wherein said composition forms a hydrogel or semi-solid mass within 120 seconds of contact with an aqueous environment.

4. The in situ gel-forming composition of claim 1, wherein said composition is an injectable liquid at a temperature in the range of about 18° C. to about 37° C.

5. The in situ gel-forming composition of claim 1, wherein said one or more polymer(s) comprise a mixture of a copolymer of lactide/trimethylene carbonate and a copolymer of lactide/glycolide.

6. The in situ gel-forming composition of claim 2, wherein said one or more bioactive agents comprise a sclerosant.

7. The in situ gel-forming composition of claim 6, wherein said sclerosant comprises polidocanol.

8. The in situ gel-forming composition of claim 5, wherein said copolymer of lactide/glycolide has a lactide/glycolide mole ratio of 60-90/40-10.

9. The in situ gel-forming composition of claim 1, wherein said blocks of poly(lactide-co-glycolide) have a lactide/glycolide mole ratio of 60-90/40-10.

* * * * *